United States Patent [19]
Habuchi et al.

[11] Patent Number: 5,910,581
[45] Date of Patent: Jun. 8, 1999

[54] POLYPEPTIDES OF GLYCOSAMINOGLYCAN SULFOTRANSFERASE ORIGINATING FROM HUMAN AND DNA CODING FOR THE POLYPEPTIDES

[75] Inventors: Osami Habuchi, Nagoya; Masakazu Fukuta, Mie-ken, both of Japan

[73] Assignee: Seikagaku Kogyo Kabushiki Kaisha, Tokyo, Japan

[21] Appl. No.: 08/899,514

[22] Filed: Jul. 24, 1997

[30] Foreign Application Priority Data

Jul. 24, 1996 [JP] Japan .................................. 8-195063

[51] Int. Cl.⁶ .............................. C12N 15/54; C12N 9/10
[52] U.S. Cl. ..................... 536/23.2; 536/23.1; 435/193; 435/252.3; 435/325; 435/320.1
[58] Field of Search ................... 536/23.1, 23.2; 435/193, 252.3, 325, 320.1

[56] References Cited

PUBLICATIONS

Fukuta M. et al. "Molecular Cloning and Expression of Chick Chondrocyte Chondroitin 6–Sulfotransferase", J. Biol. Chem. 270(31): 18575–18580, Aug. 1995.

Glycosaminoglycan Sulfotranferases in Human and Animal Sera, H. Inoue, et al., The Journal of Biological Chemistry, vol. 261, No. 10 Issue of Apr. 2, pp. 4460–4469, 1986.

*Primary Examiner*—Rebecca E. Prouty
*Attorney, Agent, or Firm*—Knobbe, Martens, Olson & Bear, LLP

[57] ABSTRACT

A polypeptide of glycosaminoglycan sulfotransferase originating from human and having the following physical and chemical properties:

(i) action: sulfate group is transferred from a sulfate group donor to N-acetylgalactosamine residue or galactose residue of glycosaminoglycan;

(ii) substrate specificity: sulfate group is transferred to the hydroxyl group position at C-6 of N-acetylgalactosamine residue of chondroitin; and sulfate group is transferred to the hydroxyl group position at C-6 of galactose residue of keratan sulfate; and (iii) molecular weight: about from 50,000 to 55,000 Da.

7 Claims, No Drawings

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 2156
        (B) TYPE: nucleic acid
        (C) STRANDEDNESS: both
        (D) TOPOLOGY: linear (ii) MOLECULE TYPE: cDNA (vi) ORIGINAL SOURCE:
        (A) ORGANISM: Human
        (B) TISSUE TYPE: Fetal brain (ix) FEATURE:
        (A) NAME/KEY: CDS
        (B) LOCATION: 147..1583
        (C) IDENTIFICATION METHOD: S (xi) SEQUENCE DESCRIPTION: SEQ ID NO:1:

```
GCGGAGGGTC GGGGCCGCCG GTGGAGTCTC GGCGGCCGGG GACAAGGGTG TCCCCCACCT      60

GAAGACGGCA AGCTGGGTCC TGAGTGATGC CCCTCAGCTG AGTGTCCAAG GCTGGCCCGA     120

GGAGCCCCAC GGCCCCACCT TTCCCC ATG GAG AAA GGA CTC ACT TTG CCC CAG     173
                             Met Glu Lys Gly Leu Thr Leu Pro Gln
                              1               5

GAC TGC CGG GAC TTT GTG CAC AGC CTG AAG ATG AGA AGC AAA TAC GCC     221
Asp Cys Arg Asp Phe Val His Ser Leu Lys Met Arg Ser Lys Tyr Ala
 10              15                  20                  25

CTT TTC TTG GTT TTT GTG GTG ATA GTT TTT GTC TTC ATC GAA AAG GAA     269
Leu Phe Leu Val Phe Val Val Ile Val Phe Val Phe Ile Glu Lys Glu
                 30                  35                  40

AAT AAA ATC ATA TCA AGG GTC TCA GAC AAG CTG AAG CAG ATT CCC CAA     317
Asn Lys Ile Ile Ser Arg Val Ser Asp Lys Leu Lys Gln Ile Pro Gln
             45                  50                  55

GCT CTA GCA GAT GCC AAC AGC ACC GAC CCA GCC CTG ATC TTA GCT GAG     365
Ala Leu Ala Asp Ala Asn Ser Thr Asp Pro Ala Leu Ile Leu Ala Glu
         60                  65                  70

AAC GCA TCT CTC TTG TCC CTG AGC GAG CTC GAT TCA GCC TTC TCC CAG     413
Asn Ala Ser Leu Leu Ser Leu Ser Glu Leu Asp Ser Ala Phe Ser Gln
     75                  80                  85

CTT CAG AGC CGT CTC CGC AAC CTC AGC TTG CAG CTG GGC GTG GAG CCA     461
Leu Gln Ser Arg Leu Arg Asn Leu Ser Leu Gln Leu Gly Val Glu Pro
 90                  95                 100                 105

GCC ATG GAG GCC GCA GGG GAG GAA GAG GAA GAG CAG AGA AAG GAG GAG     509
Ala Met Glu Ala Ala Gly Glu Glu Glu Glu Glu Gln Arg Lys Glu Glu
                110                 115                 120

GAG CCG CCC AGA CCG GCC GTG GCG GGG CCC CGG CGC CAC GTG CTG CTC     557
Glu Pro Pro Arg Pro Ala Val Ala Gly Pro Arg Arg His Val Leu Leu
            125                 130                 135

ATG GCC ACC ACG CGC ACC GGC TCC TCG TTC GTG GGC GAG TTC TTC AAC     605
Met Ala Thr Thr Arg Thr Gly Ser Ser Phe Val Gly Glu Phe Phe Asn
        140                 145                 150

CAG CAG GGC AAC ATC TTC TAC CTC TTC GAG CCG CTG TGG CAC ATC GAG     653
Gln Gln Gly Asn Ile Phe Tyr Leu Phe Glu Pro Leu Trp His Ile Glu
    155                 160                 165

CGC ACA GTG TCC TTC GAG CCG GGG GGC GCC AAC GCC GCG GGC TCG GCC     701
Arg Thr Val Ser Phe Glu Pro Gly Gly Ala Asn Ala Ala Gly Ser Ala
170                 175                 180                 185
```

```
CTG GTG TAC CGC GAC GTG CTC AAG CAG CTC TTC CTG TGC GAC CTG TAC     749
Leu Val Tyr Arg Asp Val Leu Lys Gln Leu Phe Leu Cys Asp Leu Tyr
            190                 195                 200

GTG CTG GAG CAC TTC ATC ACG CCG CTG CCC GAG GAC CAC CTG ACT CAG     797
Val Leu Glu His Phe Ile Thr Pro Leu Pro Glu Asp His Leu Thr Gln
            205                 210                 215

TTC ATG TTC CGC CGG GGC TCC AGC CGC TCC CTG TGC GAG GAC CCC GTC     845
Phe Met Phe Arg Arg Gly Ser Ser Arg Ser Leu Cys Glu Asp Pro Val
            220                 225                 230

TGT ACG CCC TTC GTC AAG AAG GTC TTC GAG AAG TAC CAC TGC AAG AAC     893
Cys Thr Pro Phe Val Lys Lys Val Phe Glu Lys Tyr His Cys Lys Asn
            235                 240                 245

CGC CGC TGC GGC CCC CTC AAC GTG ACG CTG GCC GCA GAG GCC TGC CGC     941
Arg Arg Cys Gly Pro Leu Asn Val Thr Leu Ala Ala Glu Ala Cys Arg
250             255                 260                 265

CGC AAG GAG CAC ATG GCC CTC AAG GCG GTG CGC ATC CGG CAG CTG GAG     989
Arg Lys Glu His Met Ala Leu Lys Ala Val Arg Ile Arg Gln Leu Glu
            270                 275                 280

TTC CTG CAG CCG CTG GCC GAG GAC CCC CGC CTG GAC CTG CGC GTC ATC    1037
Phe Leu Gln Pro Leu Ala Glu Asp Pro Arg Leu Asp Leu Arg Val Ile
            285                 290                 295

CAG CTG GTG CGC GAC CCC CGG GCC GTG CTG GCC TCG CGC ATG GTG GCC    1085
Gln Leu Val Arg Asp Pro Arg Ala Val Leu Ala Ser Arg Met Val Ala
            300                 305                 310

TTC GCC GGC AAG TAT AAG ACC TGG AAG AAG TGG CTG GAC GAC GAG GGC    1133
Phe Ala Gly Lys Tyr Lys Thr Trp Lys Lys Trp Leu Asp Asp Glu Gly
            315                 320                 325

CAG GAC GGC CTG AGG GAA GAG GAG GTG CAG CGG CTG CGG GGC AAC TGC    1181
Gln Asp Gly Leu Arg Glu Glu Glu Val Gln Arg Leu Arg Gly Asn Cys
330             335                 340                 345

GAG AGC ATC CGC CTG TCC GCG GAG CTG GGG CTG CGG CAG CCC GCC TGG    1229
Glu Ser Ile Arg Leu Ser Ala Glu Leu Gly Leu Arg Gln Pro Ala Trp
            350                 355                 360

CTG CGG GGC CGC TAC ATG CTG GTG CGC TAC GAG GAC GTG GCA CGC GGG    1277
Leu Arg Gly Arg Tyr Met Leu Val Arg Tyr Glu Asp Val Ala Arg Gly
            365                 370                 375

CCG CTG CAG AAG GCC CGC GAG ATG TAC CCG TTC GCC GGC ATC CCC CTG    1325
Pro Leu Gln Lys Ala Arg Glu Met Tyr Pro Phe Ala Gly Ile Pro Leu
            380                 385                 390

ACC CCG CAG GTG GAA GAC TGG ATC CAA AAG AAC ACG CAG GCG GCC CAC    1373
Thr Pro Gln Val Glu Asp Trp Ile Gln Lys Asn Thr Gln Ala Ala His
            395                 400                 405

GAC GGC AGC GGC ATC TAC TCC ACG CAG AAG AAC TCC TCG GAG CAG TTC    1421
Asp Gly Ser Gly Ile Tyr Ser Thr Gln Lys Asn Ser Ser Glu Gln Phe
410             415                 420                 425

GAG AAG TGG CGC TTC AGC ATG CCC TTC AAG CTG GCC CAG GTG GTG CAG    1469
Glu Lys Trp Arg Phe Ser Met Pro Phe Lys Leu Ala Gln Val Val Gln
            430                 435                 440

GCC CCG TGC GGC CCT GCC ATG CGC CTC TTC GGC TAC AAA CTG GCG CGG    1517
Ala Pro Cys Gly Pro Ala Met Arg Leu Phe Gly Tyr Lys Leu Ala Arg
            445                 450                 455

GAC GCC GCC GCC CTC ACC AAC CGC TCA GTC AGC CTG CTG GAG GAG AGG    1565
Asp Ala Ala Ala Leu Thr Asn Arg Ser Val Ser Leu Leu Glu Glu Arg
            460                 465                 470

GGC ACC TTC TGG GTC ACG TAGGGGGTC TGGGGCCGTA TGCCCTCCTT           1613
Gly Thr Phe Trp Val Thr
            475

GTGGAAAGGC CTGGGCCCGT CTTTCTGGCT GAAAGGCCTG CCCCGTCTTT CTGCCCCAGC  1673

CCTCGCAGCA GAGAGCCGGC ACAGCGCCAT GAGCGGAGCA GCGCCTCCTG TAGCAGTAGG  1733
```

```
GCCCCCAGCC AGCGCTCCAG CCAAAGCGGC GGCCCCAAGG GTTAATGTGG CGGAGAAACA      1793

GGGACAGGTG CCCGAGGTCC CCTTGGAAGG GCCATCACAC CCAGACCCAA CGGGTTGCAG      1853

CCTCCTGAGC AGGCCTAGGC AGGCCCGGGC CTGTTGGCAA GCTTCGATCT CGAACTACAA      1913

CAACCAGAAA CATACATTCG TGCCTGGAGA CCCTGCAGGC CAGAGTCCAA ATATTTAACA      1973

ATCAGAAGGG GCAAGGCTCT GACCAGTGAC AGTCAGACCT CCTGCTTTAT TTGGTGTTAA      2033

CCGTTTCTTG TCTGGATGGT GAAGTCTGGA ATCTGGGTGG GCTCCTTGGA GGAGGGGCTA      2093

GGACAGCCGT GGGTGTCAAA GGTGGCATTT GAGGCTCGTT TGAGGTGACA GTGGCTGTTT      2153

CCG                                                                   2156
```

(2) INFORMATION FOR SEQ ID NO:2:

(i) SEQUENCE CHARACTERISTICS:
        (A) LENGTH: 479
        (B) TYPE: amino acid
        (D) TOPOLOGY: linear (ii) MOLECULE TYPE: protein (xi) SEQUENCE DESCRIPTION: SEQ ID NO:2:

```
Met Glu Lys Gly Leu Thr Leu Pro Gln Asp Cys Arg Asp Phe Val His
  1               5                  10                  15

Ser Leu Lys Met Arg Ser Lys Tyr Ala Leu Phe Leu Val Phe Val Val
             20                  25                  30

Ile Val Phe Val Phe Ile Glu Lys Glu Asn Lys Ile Ile Ser Arg Val
         35                  40                  45

Ser Asp Lys Leu Lys Gln Ile Pro Gln Ala Leu Ala Asp Ala Asn Ser
     50                  55                  60

Thr Asp Pro Ala Leu Ile Leu Ala Glu Asn Ala Ser Leu Leu Ser Leu
 65                  70                  75                  80

Ser Glu Leu Asp Ser Ala Phe Ser Gln Leu Gln Ser Arg Leu Arg Asn
                 85                  90                  95

Leu Ser Leu Gln Leu Gly Val Glu Pro Ala Met Glu Ala Ala Gly Glu
            100                 105                 110

Glu Glu Glu Gln Arg Lys Glu Glu Pro Pro Arg Pro Ala Val
        115                 120                 125

Ala Gly Pro Arg Arg His Val Leu Leu Met Ala Thr Thr Arg Thr Gly
130                 135                 140

Ser Ser Phe Val Gly Glu Phe Phe Asn Gln Gly Asn Ile Phe Tyr
145                 150                 155                 160

Leu Phe Glu Pro Leu Trp His Ile Glu Arg Thr Val Ser Phe Glu Pro
                165                 170                 175

Gly Gly Ala Asn Ala Ala Gly Ser Ala Leu Val Tyr Arg Asp Val Leu
            180                 185                 190

Lys Gln Leu Phe Leu Cys Asp Leu Tyr Val Leu Glu His Phe Ile Thr
        195                 200                 205

Pro Leu Pro Glu Asp His Leu Thr Gln Phe Met Phe Arg Arg Gly Ser
    210                 215                 220

Ser Arg Ser Leu Cys Glu Asp Pro Val Cys Thr Pro Phe Val Lys Lys
225                 230                 235                 240

Val Phe Glu Lys Tyr His Cys Lys Asn Arg Arg Cys Gly Pro Leu Asn
                245                 250                 255

Val Thr Leu Ala Ala Glu Ala Cys Arg Arg Lys Glu His Met Ala Leu
            260                 265                 270
```

```
Lys Ala Val Arg Ile Arg Gln Leu Glu Phe Leu Gln Pro Leu Ala Glu
        275                 280                 285

Asp Pro Arg Leu Asp Leu Arg Val Ile Gln Leu Val Arg Asp Pro Arg
        290                 295                 300

Ala Val Leu Ala Ser Arg Met Val Ala Phe Ala Gly Lys Tyr Lys Thr
305                 310                 315                 320

Trp Lys Lys Trp Leu Asp Asp Glu Gly Gln Asp Gly Leu Arg Glu Glu
                325                 330                 335

Glu Val Gln Arg Leu Arg Gly Asn Cys Glu Ser Ile Arg Leu Ser Ala
            340                 345                 350

Glu Leu Gly Leu Arg Gln Pro Ala Trp Leu Arg Gly Arg Tyr Met Leu
                355                 360                 365

Val Arg Tyr Glu Asp Val Ala Arg Gly Pro Leu Gln Lys Ala Arg Glu
        370                 375                 380

Met Tyr Pro Phe Ala Gly Ile Pro Leu Thr Pro Gln Val Glu Asp Trp
385                 390                 395                 400

Ile Gln Lys Asn Thr Gln Ala Ala His Asp Gly Ser Gly Ile Tyr Ser
                405                 410                 415

Thr Gln Lys Asn Ser Ser Glu Gln Phe Glu Lys Trp Arg Phe Ser Met
            420                 425                 430

Pro Phe Lys Leu Ala Gln Val Val Gln Ala Pro Cys Gly Pro Ala Met
        435                 440                 445

Arg Leu Phe Gly Tyr Lys Leu Ala Arg Asp Ala Ala Ala Leu Thr Asn
450                 455                 460

Arg Ser Val Ser Leu Leu Glu Glu Arg Gly Thr Phe Trp Val Thr
465                 470                 475         479

(2) INFORMATION FOR SEQ ID NO:3:

(i) SEQUENCE CHARACTERISTICS:
        (A) LENGTH: 14
        (B) TYPE: amino acid
        (D) TOPOLOGY: linear (ii) MOLECULE TYPE: peptide (xi) SEQUENCE DESCRIPTION: SEQ ID NO:3:

Leu Val Ile Xaa Xaa Xaa Xaa Asn Asn Phe Ile Xaa Xaa Val
1               5                   10

(2) INFORMATION FOR SEQ ID NO:4:

(i) SEQUENCE CHARACTERISTICS:
        (A) LENGTH: 14
        (B) TYPE: amino acid
        (D) TOPOLOGY: linear (ii) MOLECULE TYPE: peptide (xi) SEQUENCE DESCRIPTION: SEQ ID NO:4:

Xaa Val Ile Xaa Glu Xaa Xaa Asn Asn Phe Ile Xaa Xaa Val
1               5                   10

(2) INFORMATION FOR SEQ ID NO:5:

(i) SEQUENCE CHARACTERISTICS:
        (A) LENGTH: 24
        (B) TYPE: amino acid
        (D) TOPOLOGY: linear (ii) MOLECULE TYPE: peptide (xi) SEQUENCE DESCRIPTION: SEQ ID NO:5:
```

```
Leu Val Ile Xaa Glu Lys Glu Asn Asn Phe Ile Ser Arg Val Ser Asp
 1               5                  10                  15

Lys Leu Lys Xaa Xaa Pro Xaa Val
            20
```

(2) INFORMATION FOR SEQ ID NO:6:

(i) SEQUENCE CHARACTERISTICS:
        (A) LENGTH: 13
        (B) TYPE: amino acid
        (D) TOPOLOGY: linear (ii) MOLECULE TYPE: peptide (xi) SEQUENCE DESCRIPTION: SEQ ID NO:6:

```
Ser Phe Ile Ser Pro Ala Pro Asn Asn Xaa Leu Thr Ala
 1               5                  10
```

(2) INFORMATION FOR SEQ ID NO:7:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(xi) SEQUENCE DESCRIPTION: SEQ ID NO:7:

CAAAGCTTGA RAARGARAAY AAYTTYAT                         28

(2) INFORMATION FOR SEQ ID NO:8:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(xi) SEQUENCE DESCRIPTION: SEQ ID NO:8:

MGKGTKWSKG AYAARCTNAA                               20

(2) INFORMATION FOR SEQ ID NO:9:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(xi) SEQUENCE DESCRIPTION: SEQ ID NO:9:

AARTADWSKG GKCGKGGKCT TCTTAAGCT                      29

POLYPEPTIDES OF GLYCOSAMINOGLYCAN SULFOTRANSFERASE ORIGINATING FROM HUMAN AND DNA CODING FOR THE POLYPEPTIDES

BACKGROUND OF THE INVENTION

The present invention relates to a polypeptide of glycosaminoglycan sulfotransferase originating from human and a DNA coding for the polypeptide.

Chondroitin sulfate is a representative sulfated mucopolysaccharide (glycosaminoglycan). Chondroitin sulfate proteoglycan (CSPG) exists abundantly in cartilage, and is considered to participate in expression and maintenance of the phenotype of chondrocyte (Tsukahara, T., Okamura, M., Suzuki, S., Iwata, H., Miura, T., and Kimata, K. (1991) J. Cell Sci. 100, 387–395). CSPG exists also in various tissues other than cartilage, and is considered to play an important role for intercellular interactions (Kjellen, L. and Lindahl, U. (1991) Annu. Rev. Biochem. 60, 443–475).

Major chondroitin sulfate found in mammalian and avian tissues has sulfate groups at C-6 or C-4 positions of acetylgalactosamine residues. The following knowledge has been obtained for the ratio of 6-sulfation/4-sulfation. (i) The ratio of chondroitin 6-sulfate/chondroitin 4-sulfate (6/4 ratio) increases along with progress of final differentiation of cartilage. (ii) The 6/4 ratio in CSPG decreases in skin of rat along with passage of days after the birth. (iii) When CSPG and dermatan sulfate proteoglycan (DSPG) present in arterial smooth muscle cells are compared between an atherosclerosis-resistant pigeon and an atherosclerosis-sensitive pigeon, the major component is chondroitin 4-sulfate in the former species, whereas the major component is chondroitin 6-sulfate in the latter species. (iv) When monocytic leukemia cells (Ml) are cultured under the culture condition successively changed to suit for cell proliferation, inhibition of high-density proliferation and induction of differentiation to macrophage, the 6/4 ratio in CSPG is decreasing as the condition is changed in the above-defined order, and almost only chondroitin 4-sulfate is produced under the final differentiation-inducing state. (v) As a result of comparison of human colon normal tissue with human colon tumor tissue, chondroitin 6-sulfate and chondroitin in PG are increased in the tumor tissue. (vi) When mouse osteoblast cells are compared before and after calcification, the 6/4 ratio of DSPG is decreased in the cells after calcification. (vii) When platelet derived growth factor (PDGF) is added to a culture medium of monkey arterial smooth muscle cells, the 6/4 ratio of versican-like CSPG is increased as compared with a control with no addition of PDGF (Glycobiology Series (I), "Diversified World of Saccharides", Kodansha, pp. 164, 166).

It has been also reported for chondroitin sulfate that two sulfate groups exist per repeating disaccharide unit. For example, GlcAβ1→3GalNAc(4,6-bisS) has been found in: subcultured chick embryo chondrocytes; mouse mast cells differentiated from myeloid cells cultivated in a medium supplemented with a conditioned medium derived from mouse spleen cell cultures; rat glomeruli; culture liquid of organotypic cultured human colonic mucosa; rat serosa mast cells; secretory granules of human lung mast cells; human monocytes activated by phorbol myristate acetate and macrophages derived from such monocytes; mouse osteoblasts; rat glomerulus vascular membrane cells; and sea cucumber parietal cells. In addition, GalNAc(4,6-bisS) has been found in the nonreducing terminal of the chondroitin sulfate from chick embryo epiphyseal cartilage, rat processus xiphoideus cartilage, and cell layer obtained by cultivating chick embryo chondrocyte. Further, GalNAc(4,6-bisS) β1→4GlcAβ1→3GalNAc(4,6-bisS) has been found in the nonreducing terminal of the chondroitin sulfate from thrombomodulin extracted and purified from rabbit lung. Moreover, GlcA(2S)-GalNAc(6S) has been found in the nonreducing terminal of the chondroitin sulfate from mast cells originating from mouse lymph node (Glycobiology Series (I), "Diversified World of Saccharides," Kodansha, p.166).

It is considered that the diversification of the sulfation pattern of chondroitin sulfate as described above reflects a molecular basis of the function of chondroitin sulfate. It is also considered that sulfation plays an important role in expression of physiological activities of chondroitin sulfate. Considering the importance of sulfation in expression of physiological activities of chondroitin sulfate, it is expected that a method for sulfating a specific site of chondroitin sulfate is indispensable to analyze physiological activities of chondroitin sulfate and modify its function. Sulfation at a specific site of a sugar residue of glycosaminoglycan is catalyzed by a sulfotransferase specific to the site.

If a gene of sulfotransferase for glycosaminoglycan is cloned, information on substrate specificity concerning the acceptor may be obtained, providing an approach useful to study the relationship between structure and function of glycosaminoglycan. It is assumed that various types of glycosaminoglycan sulfotransferases participate in synthesis of glycosaminoglycan. However, cloning of cDNA of sulfotransferase is difficult. In fact, those having been cloned only include cDNA's of N-sulfotransferase/N-deacetylase from rat liver, heparin-producing cell line, and mouse mast cell tumor.

The present inventors have apparently homogenously purified, from a culture supernatant of chick chondrocytes cultured in a serum-free medium, chondroitin 6-sulfotransferase (hereinafter often abbreviated as "C6ST") which transfers sulfate group from 3'-phosphoadenosine 5'-phosphosulfate to the C-6 position of N-acetylgalactosamine residue of glycosaminoglycan such as chondroitin (Habuchi, O., Matsui, Y., Kotoya, Y., Aoyama, Y., Yasuda, Y., and Noda, M. (1993) J. Biol. Chem. 268, 21968–21974). Further, the present inventors have prepared oligonucleotide primers on the basis of the partial amino acid sequence of this enzyme, performed the chick cDNA cloning with the aid of the primers and proved that C6ST activity is expressed by the polypeptide obtained from this DNA. The present inventors have also found that this enzyme has an activity to transfer sulfate group to the C-6 position of galactose residue of keratan sulfate (Fukuta, M., Uchimura, K., Nakashima, K., Kato, M., Kimata, K., Shinomura, T. and Habuchi, O. (1995) J. Biol. Chem. 270, 18575–18580).

However, it has been yet unknown of the DNA that codes for the polypeptide of chondroitin 6-sulfotransferase originating from human the application of which to pharmaceuticals may be expected.

Considering the importance of sulfation in expression of physiological activities of chondroitin sulfate, the enzyme, which transfers sulfate group to chondroitin sulfate, is extremely important not only to perform a study on analysis of function of chondroitin sulfate but also to provide a certain type of chondroitin sulfate in order to create pharmaceuticals having physiological activities preferred for human. Moreover, if polypeptide of chondroitin 6-sulfotransferase (C6ST) originating from human and DNA coding for the polypeptide are obtained, the medical application thereof, including gene therapy, might be expected in the form of pharmaceuticals against, or diagnostics of, human diseases attributable to a low sulfation at C-6 position of N-acetylgalactosamine residue of chondroitin sulfate, a low sulfation at C-6 position of galactose residue of keratan sulfate and the like ("low sulfation" as used herein means that the sulfation degree is low).

SUMMARY OF THE INVENTION

The main object of the present invention is, therefore, to provide a polypeptide of glycosaminoglycan sulfotransferase originating from human and a partial polypeptide thereof as well as a DNA coding for at least a part of the glycosaminoglycan sulfotransferase originating from human.

The present inventors have performed the cloning of cDNA that codes for chick chondroitin 6-sulfotransferase and, by using a fragment derived from this cDNA, succeeded in cloning of cDNA coding for this enzyme from human cDNA library. Based on this, the present inventors have provided a polypeptide of glycosaminoglycan sulfotransferase originating from human and a partial polypeptides thereof (hereinafter collectively referred to as "polypeptide of the present invention") as well as a DNA coding for at least a part of glycosaminoglycan sulfotransferase originating from human (hereinafter also referred to as "DNA of the present invention").

Thus, according to one aspect of the present invention, there is provided a polypeptide of glycosaminoglycan sulfotransferase originating from human and having the following physical and chemical properties:

(i) action: sulfate group is transferred from a sulfate group donor to N-acetylgalactosamine residue or galactose residue of glycosaminoglycan;

(ii) substrate specificity: sulfate group is transferred to the hydroxyl group position at C-6 of N-acetylgalactosamine residue of chondroitin; and sulfate group is transferred to the hydroxyl group position at C-6 of galactose residue of keratan sulfate; and (iii) molecular weight: about from 50,000 to 55,000 Da.

According to another aspect of the present invention, there is provided a polypeptide of glycosaminoglycan sulfotransferase originating from human and having at least a part of the amino acid sequence shown in SEQ ID NO:2, with or without substitution, deletion or insertion of one or more amino acid residues which do not substantially deteriorate the activity to transfer sulfate group from a sulfate group donor to N-acetylgalactosamine residue or galactose residue of glycosaminoglycan. In a preferred embodiment, the present invention provides a polypeptide of glycosaminoglycan sulfotransferase originating from human and having at least a part of the amino acid sequence shown in SEQ ID NO:2.

According to another aspect, the present invention provides a polypeptide including a part of the above-defined polypeptide.

According to still another aspect of the present invention, there is provided a DNA coding for at least a part of the above-defined polypeptide of glycosaminoglycan sulfotransferase. The DNA of the present invention includes preferably a DNA having a nucleotide sequence coding for an amino acid sequence represented by amino acids numbered from 1 to 479 or 20 to 479 in SEQ ID NO:2, and more preferably a DNA having at least a part or the whole of the nucleotide sequence shown in SEQ ID NO:1.

Since a DNA coding for glycosaminoglycan sulfotransferase, originating from human has been obtained, it can be expected to produce the glycosaminoglycan sulfotransferase originating from human in quantities sufficient to make the enzyme industrially available. It can also be expected the application of human-originated glycosaminoglycan sulfotransferase cDNA and C6ST enzyme protein to medical use.

DETAILED DESCRIPTION OF THE INVENTION

The present invention will now be explained in detail successively in connection with the polypeptide and the DNA of the present invention.

<1> Polypeptide of the Present Invention

The polypeptide of the present invention includes a polypeptide of glycosaminoglycan sulfotransferase originating from human (hereinafter also referred to as human glycosaminoglycan sulfotransferase) and having the following physical and chemical properties:

(i) action: sulfate group is transferred from a sulfate group donor to N-acetylgalactosamine residue or galactose residue of glycosaminoglycan;

(ii) substrate specificity: sulfate group is transferred to the hydroxyl group position at C-6 of N-acetylgalactosamine residue of chondroitin; sulfate group is transferred to the hydroxyl group position at C-6 of galactose residue of keratan sulfate; and (iii) molecular weight: about from 50,000 to 55,000 Da.

The sulfate group donor is preferably 3'-phosphoadenosine 5'-phosphosulfate.

A preferred polypeptide of the present invention is a type II membrane protein.

The above-defined molecular weight is an estimated molecular weight of a polypeptide calculated on the basis of amino acid sequence. This enzyme is expected to exist as glycoprotein in nature and hence to have a larger molecular weight than that above-defined as a result of the addition of sugar chain.

The "type II membrane protein" means a protein which contains hydrophobic transmembrane domain at amino terminal side and which is biosynthesized in such a shape that carboxyl terminal is projecting into lumen of Golgi body.

The polypeptide of the present invention, in addition to have the physical and chemical properties as defined above in (i) to (iii), is preferred to have 460 to 479 amino acid residues.

As regards the substrate specificity as defined above in (ii), the polypeptide of the present invention exhibits not only an activity to transfer sulfate group to the C-6 position of N-acetylgalactosamine (C6ST activity), but also an activity to transfer sulfate group to the C-4 position thereof (C4ST activity), and the ratio of the former activity (C6ST activity) to the latter activity (C4ST activity) is about 15 to 20.

In another aspect, the polypeptide of the present invention includes the polypeptide of human glycosaminoglycan sulfotransferase which may optionally have substitution, deletion or insertion of one or more amino acid residues which do not substantially deteriorate the activity to transfer sulfate group from a sulfate group donor to N-acetylgalactosamine residue or galactose residue of glycosaminoglycan. The polypeptide of the present invention preferably has at least a part of the amino acid sequence having not less than 80% (more preferably, not less than 90%) of homology with the amino acid sequence shown in SEQ ID NO:2, more preferably at least a part of the amino acid sequence shown in SEQ ID NO:2 including no substitution, deletion or insertion of amino acid residue.

Such substitution, deletion or insertion of amino acid residues can be obtained by introducing one or more nucleotides responsible for substitution, deletion or insertion of one or more amino acid residues into a DNA that codes for at least a part of the amino acid sequence shown in SEQ ID NO:2 and then by expressing the resultant DNA.

Substitution, deletion or insertion of nucleotides can be introduced into a DNA sequence by synthesizing a sequence that has restriction enzyme cleavage terminals at both ends and contain a portion stretching over both sides of a mutation point, followed by replacing the corresponding portion of non-mutated DNA sequence with the synthesized sequence. Alternatively, substitution, insertion or deletion can be introduced into a DNA sequence in accordance with a method such as a site-specific mutagenesis method (Kramer, W. and Frits, H. J., Meth. in Enzymol., 154, 350(1987); Kunkel, T. A. et al., Meth. in Enzymol., 154, 367(1987)). The activity to transfer sulfate group from a sulfate group donor to N-acetylgalactosamine residue or galactose residue of glycosaminoglycan can be determined by e.g. enzyme activity assay as described below, and consequently, substitution, deletion or insertion of one of more amino acid residues which doesn't substantially deteriorate the activity can be easily recognized by those skilled in the art.

Also, it is possible to change part of the structure of the polypeptide by natural or artificial mutation without significant change of the activity of the polypeptide. The polypeptide of the present invention includes a polypeptide having a structure corresponding to homologous variants of the polypeptide having the amino acid sequence shown in SEQ ID NO:2.

The amino acid sequence shown in SEQ ID NO:2 contains methionine at the amino acid number 20 which, in common with methionine at the amino acid number 1, may possibly form N-terminal of the polypeptide of the present invention. Hence, the polypeptide of the present invention includes the polypeptides of glycosaminoglycan sulfotransferase having amino acid sequences represented by amino acids numbered from 1 to 479 and from 20 to 479 in SEQ ID NO:2, both of which are particularly preferred. $NH_2$-terminal signal peptide sequence is apparently absent in the amino acid sequence shown in SEQ ID NO:2, but the presence of this signal peptide sequence need not always to be excluded. Irrespective of either methionine constitutes N-terminal and irrespective of whether $NH_2$-terminal signal peptide sequence is present or absent, the amino acid sequence shown in SEQ ID NO:2 contains glycosaminoglycan sulfotransferase polypeptides.

Based on these viewpoints, "having at least a part of the amino acid sequence shown in SEQ ID NO:2" as used herein refers to having the shortest amino acid sequence necessary for a polypeptide to have sulfotransferase activity.

Further, the polypeptide of the present invention includes the polypeptide which contains a part of the above-defined polypeptides. The "part" as herein used refers to a part having some activity or function such as sulfotransferase activity or antigenicity. Such part may be easily recognized by those skilled in the art.

The polypeptide of the present invention need not always to exist as independent polypeptides, but may form part of a fusion protein. Fusion polypeptides which may be mentioned are those containing a polypeptide of the present invention together with one or more other polypeptides required for expression.

The polypeptide of the present invention as discussed above can be prepared by using the DNA of the present invention in a manner as described below. More specifically, glycosaminoglycan sulfotransferase (C6ST) can be prepared by culturing a cell harboring a DNA of the present invention in an appropriate medium to allow C6ST to be produced and accumulated in the medium, and then by collecting C6ST from the medium. The DNA of the present invention can be expressed with the aid of a host-vector system commonly used for producing proteins. Mammalian cells such as COS-7 cells are preferred. As for the expression, the DNA of the present invention may be directly expressed, or it may be expressed as a fusion protein containing another protein. The DNA of the present invention may be expressed in its entire length, or a part of it may be expressed as a partial peptide.

An antibody for binding C6ST can be prepared by using the polypeptide of C6ST obtained in a manner as described above, the partial polypeptide thereof, or a fusion protein of any of them with another protein. The preparation of antibody may be performed in the same manner as in preparation of an ordinary antibody. A monoclonal antibody for binding C6ST also can be prepared in accordance with an ordinary method.

<2> DNA of the Present Invention

The DNA of the present invention is a DNA originating from human and having been isolated for the first time according to the present invention, which codes for at least a part of the polypeptide of human chondroitin 6-sulfotransferase.

More specifically, the DNA of the present invention includes a DNA coding for at least a part of the polypeptide of human C6ST and having the following physical and chemical properties:

(i) action: sulfate group is transferred from a sulfate group donor to N-acetylgalactosamine residue or galactose residue of glycosaminoglycan;

(ii) substrate specificity: sulfate group is transferred to the hydroxyl group position at C-6 of N-acetylgalactosamine residue of chondroitin; sulfate group is transferred to the hydroxyl group position at C-6 of galactose residue of keratan sulfate; and (iii) molecular weight: about from 50,000 to 55,000 Da.

The sulfate group donor is preferably 3'-phosphoadenosine 5'-phosphosulfate.

A preferred polypeptide is a type II membrane protein.

In addition to having the physical and chemical properties as defined above in (i) to (iii), polypeptides are preferred to have 460 to 479 amino acid residues.

As regards the substrate specificity defined above in (ii), the polypeptide of the present invention has not only an activity to transfer sulfate group to the C-6 position of N-acetylgalactosamine (C6ST activity), but also an activity to transfer sulfate group to the C-4 position thereof (C4ST activity), and the ratio of the former activity (C6ST activity) to the latter activity (C4ST activity) is about 15 to 20.

The enzyme encoded by the DNA of the present invention has the activity to transfer sulfate group to the hydroxyl group position at C-6 of N-acetylgalactosamine of chondroitin, and consequently, is conveniently called "chondroitin 6-sulfotransferase". In this specification also, this enzyme is referred to as "chondroitin 6-sulfotransferase" or as "C6ST" in abbreviated form.

The nucleotide sequence of the DNA of the present invention is not specifically limited, provided that it codes for at least a part of the polypeptide of the glycosaminoglycan sulfotransferase.

The DNA of the present invention includes a DNA that codes for at least a part of the polypeptide of human glycosaminoglycan sulfotransferase and codes for the whole or a part of the amino acid sequence shown in SEQ ID NO:2.

And, the polypeptide of human glycosaminoglycan sulfotransferase encoded by the DNA of the present invention may optionally contain substitution, deletion or insertion of one or more amino acid residues which do not substantially deteriorate the activity to transfer sulfate group from a sulfate group donor to N-acetylgalactosamine residue or galactose residue of glycosaminoglycan.

DNA's of the present invention which may be specifically mentioned are those having nucleotide sequences coding for amino acid sequences represented by amino acids numbered from 1 to 479 and from 20 to 479 in SEQ ID NO:2, both of which are particularly preferred. In another aspect, the DNA of the present invention is preferably one having at least a part or the whole of the nucleotide sequence shown in SEQ ID NO:1. The nucleotide sequence shown in SEQ ID NO:1 contains another methionine codon (ATG) at the position corresponding to the amino acid numbered 20. Of these methionine codons, the first methionine codon is the more possibly to constitute an initiation codon, but the other may also be possible to act as an initiation codon. Thus, DNA's which may be specifically mentioned are DNA having a nucleotide sequence ranging from 147 to 1583 of SEQ ID NO:1, DNA having a nucleotide sequence ranging from 204 to 1583 of SEQ ID NO:1 and the like.

Those skilled in the art will readily understand that DNA's having different nucleotide sequences due to degeneracy of genetic codes are also included in the DNA of the present invention. Such DNA's are all included in the DNA of the present invention.

Still more, chromosomal glycosaminoglycan sulfotransferase gene is supposed to contain one or more introns in the coding region thereof. A DNA fragment, even if it is divided into segments due to the presence of such introns, may be included in the DNA fragment of the present invention, provided that it codes for at least a part of a polypeptide of glycosaminoglycan sulfotransferase. More specifically, it should be understood that the term "code" as herein used means that a DNA has a nucleotide sequence which can be subjected to various processings on transcription to finally produce an intended polypeptide.

The expression "code for at least a part of polypeptide" as herein used means to code for a part having one or more activities or functions, e.g. sulfotransferase activity, antigenicity and the like, or codes for a part to which the corresponding nucleotide sequence is specific to the glycosaminoglycan sulfotransferase, thus usable as a primer or a probe.

The present invention includes further a DNA or RNA complementary to the DNA of the present invention. The DNA of the present invention may be a single-stranded DNA comprising only a C6ST encoding strand, or it may be a double-stranded DNA composed of the single strand and a DNA or RNA strand having a sequence complementary thereto.

The DNA of the present invention may have an entire length of a coding region which codes for the entire C6ST, or it may be a fragment which codes for a partial peptide of C6ST.

The DNA of the present invention, since the nucleotide sequence thereof having been determined in accordance with the present invention, can be obtained by synthesizing on the basis of the nucleotide sequence or by amplifying a human chromosomal DNA or RNA according to PCR method (Polymerase Chain Reaction method) using the oligonucleotide primers prepared on the basis of the sequence. As discussed hereinafter in examples, the DNA of the present invention has been obtained for the first time by means of cDNA cloning comprising the following steps:

(1) Cloning of a cDNA which codes for chick C6ST polypeptide:
 (i) Determination of a partial amino acid sequence of C6ST purified from chick embryo chondrocyte;
 (ii) Preparation of an oligonucleotide primer for PCR on the basis of the determined amino acid sequence;
 (iii) Amplification of a partial cDNA of C6ST from poly(A)+ RNA derived from chick embryo chondrocytes in accordance with the PCR method; and
 (iv) Screening of the entire length cDNA of C6ST from cDNA library derived from chick embryo chondrocytes.

(2) Cloning of a cDNA which codes for human C6ST polypeptide:
 (i) Preparation of a probe for screening human cDNA library on the basis of results of nucleotide sequence analysis of the cDNA isolated in a manner as described above in (iv);
 (ii) Screening of cDNA clone that codes for human C6ST by using the probe prepared as described in (i); and
 (iii) Nucleotide sequence analysis of the obtained cDNA.

DNA production process of the present invention is by no means limited to those described above, but the above-cited PCR method or any of other known cDNA cloning methods may be used.

A method of obtaining the DNA of the present invention will be specifically explained below.

(1) Determination of Partial Amino Acid Sequence of Chick C6ST and Preparation of PCR Primers (i) Purification of Chick C6ST The chondroitin 6-sulfotransferase can be purified from cultured cells expressing this enzyme, such as chick embryo chondrocytes, by using a combination of commonly known protein purification method and commonly known sulfotransferases purification method. Preferably, purification can be performed as described in J. Biol. Chem. 268, (29), 21968–21974 (1993). A method of measuring the activity of sulfotransferase and a method of determining the position of a transferred sulfate group is described in detail under the caption of "enzyme activity assay" at the beginning of the description of examples.

(ii) Determination of Partial Amino Acid Sequence of Chick C6ST

It is known that a sugar chain is bound to purified C6ST. Accordingly, in order to remove the sugar chain, purified C6ST is digested with a sugar chain-degrading enzyme such as N-glycanase. The resultant deglycosylated C6ST is subjected to separation process such as SDS-PAGE (SDS-polyacrylamide gel electrophoresis), followed by transfer onto a polyvinylidene fluoride (PVDF) membrane, a nitrocellulose membrane or the like. The membrane is stained with a dye for staining proteins, such as Coomassie Brilliant Blue or Amido Black. A protein band formed after the digestion with N-glycanase is excised, and it is used for determining an amino acid sequence of deglycosylated C6ST. In case of the determination of an internal amino acid sequence of C6ST is necessary, deglycosylated C6ST is subjected to separation process such as SDS-PAGE or the like. The gel is stained with a dye for staining proteins, such as Coomassie Brilliant Blue or Amido Black. A protein band formed after the digestion with N-glycanase is excised, and it is used for fragmentation.

The method of fragmentation is not particularly limited, but preferably it is performed with the aid of a proteolytic enzyme such as protease V8 (sequencing grade, produced by Boehringer Mannheim). Alternatively, the excised gel may be exposed to the proteolytic enzyme, followed by separation by means of SDS-PAGE or the like. A convenient operation which may be mentioned is a method described by Cleveland, D. W., Fischer, S. G., Kirshner, M. W. and Laemmli, U. K. (1977) in J. Biol. Chem. 252, 1102–1106. In brief, this method comprises the steps of excising a protein band, inserting it into a well of another gel, placing a buffer containing a proteolytic enzyme on the inserted gel to perform SDS-PAGE, temporarily stopping electrophoresis by turning-off the power source before a forward end of a dye enters a separating gel, performing enzymatic digestion for about 30 minutes, and then starting electrophoresis again. This method is convenient in that the enzymatic digestion and the separation of peptide fragments obtained after the digestion can be performed in one-step operation. Peptides formed by the protease digestion are transferred onto a PVDF membrane, a nitrocellulose membrane or the like. The membrane is stained with a dye for staining proteins, such as Coomassie Brilliant Blue or Amido Black. After that, peptide bands are excised. The PVDF membrane, the nitrocellulose membrane or the like that contains the peptides generated after the digestion with the proteolytic enzyme can be treated by known method to determine amino terminal sequences of the peptides.

(iii) Synthesis of Oligonucleotide Primers

Once the partial amino acid sequence of C6ST is determined, oligonucleotide primers for PCR can be prepared on the basis of the amino acid sequence. It is preferable to use a region in the amino acid sequence having degeneracy as less as possible.

Examples of such primers are sense primers (primer 1s and primer 2s) and an antisense primer (primer 3a) as shown in Table 2 set forth hereinafter in Examples. The sense primer 1s and the antisense primer 3a have a sequence containing respectively a HindIII site and an EcoRI site at respective 5'-end. This allows more convenient operation of inserting a PCR-amplified DNA fragment into a vector.

The determination of partial amino acid sequence of C6ST derived from chick embryo chondrocyte and the synthesis of oligonucleotide primers for PCR are disclosed in the documents such as J. Biol. Chem. 270, 18575–18580 (1995).

(2) Preparation of Partial cDNA of C6ST (i) Preparation of Total RNA

Total RNA can be obtained in accordance with a known method (for example, Kingston, R. E., (1991) in Current Protocols in Molecular Biology, Suppl. 14, Unit 4.2, Greene Publishing Associates and Wiley Interscience, New York). The material for total RNA preparation is not particularly limited provided that mRNA of the chondroitin 6-sulfotransferase is expressed in the material. However, cell lines are preferred because they are easily handled and capable of proliferation. Among cell lines, chick embryo chondrocytes are especially preferred. The chondrocytes can be cultured in accordance with a known method (for example, Kim. J. J. and Conrad, H. E. (1976) J. Biol. Chem. 251, 6210–6217; Kim. J. J. and Conrad, H. E. (1977) J. Biol. Chem. 252, 8292–8299; Kim. J. J. and Conrad, H. E. (1980) J. Biol. Chem. 255, 1586–1597). The medium is not specifically limited provided that cell lines can grow in the medium. However, Dulbecco's Modified Eagle's medium or the like is preferred because it is well used in ordinary culture, it is easily available, and it allows the cell lines to grow therein. The medium is preferably adjusted to have a pH in a neutral region, especially at pH 7.0. D-Glucose is preferably added to the medium in an amount of about 2 g/l. In order to avoid growth of microorganisms, antibiotics such as penicillin and streptomycin are preferably added to the medium. Fetal bovine serum is preferably added to the medium in an amount of 10%.

The cells may be cultured in the same manner as in ordinary cell lines by using the medium as described above and using roller bottles or glass- or plastic-made culture dishes. The cells are preferably cultured in a carbon dioxide gas incubator. The concentration of carbon dioxide gas is preferably adjusted at 5 to 7%, and air is preferably adjusted at 97 to 93% in the incubator. The temperature is preferably adjusted at about 36 to 38° C.

Total RNA can be obtained from the cells cultured as described above in accordance with a method ordinarily used for preparing total RNA. However, total RNA is preferably prepared in accordance with a guanidine thiocyanate/CsCl method (Kingston, R. E., (1991) in Current Protocols in Molecular Biology, Suppl. 14, Unit 4.2, Greene Publishing Associates and Wiley Interscience, New York).

(ii) Preparation of Poly(A)+ RNA

Poly(A)+ RNA can be purified from the total RNA obtained as described above by means of, for example, oligo-(dT) cellulose column chromatography.

(iii) Amplification of Partial cDNA of C6ST by PCR Method

Partial cDNA of C6ST can be amplified in accordance with reverse transcription PCR (polymerase chain reaction) by using the above obtained poly(A)+ RNA as a template and using the oligonucleotide primers. PCR may be performed in a commonly known manner and according to the procedure specified in the following: a buffer (final volume 20 $\mu$l) containing the poly(A)+ RNA (1 $\mu$g), oligonucleotide 3a (50 pmol), four different deoxynucleoside triphosphates (each 500 $\mu$M), M-MLV reverse transcriptase (200 units, produced by Gibco BRL), dithiothreitol (1 mM), and RNase inhibitor (120 units, produced by Takara Shuzo) is incubated at 37° C. for 60 minutes to synthesize cDNA primary strand. After that, a reaction solution (final volume: 100 $\mu$l) containing the above-defined reaction mixture for reverse transcription (10 $\mu$l), the oligonucleotide primers (50 pmol of each of the sense and antisense primers), four different deoxynucleoside triphosphate (each 100 $\mu$M), and Taq polymerase (2.5 units) is subjected to amplification cycle. Each cycle is composed of 1 minute at 94° C., 1 minute at 45° C. and 3 minutes at 55° C. and this cycle is repeated 30 times.

Partial cDNA thus obtained can be used as a hybridization probe for screening entire length cDNA (cDNA containing entire length of a coding region) from a cDNA library.

(3) Preparation of cDNA Library (i) Synthesis of cDNA and Preparation of Recombinant DNA cDNA can be synthesized by means of a reverse transcriptase reaction using poly(A)+ RNA as a template. It is convenient to use a commercially available kit for cDNA synthesis. By using TimeSaver cDNA synthesis kit (Pharmacia LKB Biotechnology) for example, it is possible to synthesize cDNA and ligate the cDNA into a cloning vector (for example, EcoRI-digested λgt11). In the present invention also, it is preferable to use EcoRI-digested λgt11. As for the primer for the reverse transcriptase reaction, it is preferable to use random oligonucleotide primers. Recombinant DNA, which is obtained by ligating the cDNA into a cloning vector, is introduced into a host bacterial cell (transfection). Host bacterial cells should be selected depending on the selected cloning vector. And, a combination of *Escherichia coli* (*E. coli*) and a cloning vector to use *E. coli* as a host is most commonly used.

The transfection is usually performed by mixing recombinant DNA with *E. coli* in which the permeability of cell membrane has been changed in the presence of 30 mM calcium chloride. In the case of a λ phage vector such as λgt11, recombinant DNA can be directly introduced into calcium chloride-treated *E. coli*. However, in an ordinarily used method, recombinant DNA is previously in vitro encapsulated into outer coat of the phage (referred to as "in vitro packaging") so that *E. coli* is efficiently infected therewith. A kit for this purpose is also commercially available (for example, Gigapack II packaging extract, produced by Stratagene). In the present invention also, this method is preferable.

In vitro packaged recombinant DNA is transfected to *E. coli*. Suitable *E. coli* strain should be selected depending on a cloning vector to be used. Namely, when a cloning vector containing an antibiotic resistant gene is used, *E. coli* resistant to the corresponding antibiotic cannot be used. When a cloning vector containing a gene such as β-galactosidase gene (lacz) is used, it is necessary to select an *E. coli* strain which expresses no β-galactosidase activity. This is essential for screening of *E. coli* transfected with a recombinant DNA. For example, when λgt11 is used as a cloning vector, it is adequate to select an *E. coli* strain such as *E. coli* Y1088 which expresses no β-galactosidase activity.*E. coli* which had been transformed with a recombinant vector can be screened on the basis of an acquired resistance to antibiotic and an acquired β-galactosidase activity. More specifically, *E. coli* cells are plated on an agar medium and the grown colonies may be selected. The grown colonies of *E. coli* (*E. coli* transfected with the recombinant DNA) form a cDNA library. When λgt11 is used as a vector, it may be suspended in a soft agar medium together with indicator bacterial cells, and the suspension may be layered on an agar medium to form plaques. Phage plaques harboring the vector with the inserted DNA fragment express no β-galactosidase activity, and hence they can be easily selected.

(ii) Cloning of Entire Length cDNA of C6ST

Next, from the cDNA library obtained as described above, a phage clone having entire length cDNA of C6ST can be selected by means of hybridization using a partial C6ST cDNA as a probe. The hybridization may be performed in accordance with an ordinary method.

C6ST cDNA can be excised by preparing a phage DNA from the selected positive clone and by cleaving the phage DNA with suitable restriction enzyme. The obtained cDNA can be used as such, or after subcloned into an appropriate plasmid, to determine the nucleotide sequence.

(4) Cloning of cDNA that Codes for Human C6ST Polypeptide (i) Preparation of Hybridization Probes The non-human C6ST cDNA obtained as described above can be subjected to the random primer labeling with [α-$^{32}$P] dCTP to obtain a radioactive probe useful for screening of cDNA library. In brief, the aforesaid chick cDNA, together with [α-$^{32}$P] dCTP (available from Amersham) and DNA random labeling kit (available from Takara Shuzo Inc.), can be subjected to random oligonucleotide-primed labeling method (Feinberg, A. P., and Vogelstein. B. (1983) Anal. Biochem. 132, 6–13) to obtain a radiolabeled DNA probe.

(ii) Construction of Human cDNA Library

Human tissues or cells can be treated to prepare a total RNA, which then can be processed to prepare a poly(A)+ RNA. Human cDNA can be synthesized through reverse transcriptase reaction using the poly(A)+ RNA as a template. Every operation can be performed in accordance with any of the methods commonly used in genetic engineering. More specifically, these operations may be performed in a manner similar to those described above in the sections (2) and (3).

The cDNA is ligated into cloning vector. Suitable cloning vector includes, but is not limited to, EcoRI-digested λgt11. Alternatively, commercially available human cDNA ligated into cloning vector may be used. Human fetal brain cDNA library (available from Clontech) integrating a lambda vector, λgt11, is particularly preferred.

(iii) Screening of cDNA Clone Coding for Human C6ST

Among human cDNA library obtained as described above, phage clone harboring the entire length C6ST cDNA can be selected through hybridization using the [α-$^{32}$P] dCTP-labeled radioactive probe prepared in accordance with the procedure described above in (i). Hybridization can be performed by commonly used techniques in genetic engineering, e.g. plaque hybridization. A plaque which is forming a hybrid with the probe can be isolated as a positive clone through the detection of probe-ligated label.

(iv) Nucleotide Sequence Analysis of cDNA

C6ST cDNA can be excised by preparing a phage DNA from the selected positive clone and by cleaving the phage DNA with suitable restriction enzyme. The obtained cDNA can be used as such, or after subcloned into an appropriate plasmid, to determine the nucleotide sequence.

Of the nucleotide sequence of human C6ST cDNA determined in a manner as described above, the open reading frame portion is shown in SEQ ID NO:1 and the amino acid sequence is shown in SEQ ID No:2. A single open reading frame initiating with the first ATG codon suggests a protein having 479 amino acid residues and a molecular weight of 54,610.

DNA which can be obtained in a manner as described above may optionally contain substitution, deletion or insertion of one or more amino acid residues provided that the C6ST coded by this DNA doesn't substantially deteriorate the activity to transfer sulfate group from a sulfate donor to N-acetylgalactosamine residue or galactose residue of glycosaminoglycan. Such substitution, deletion or insertion of amino acid residues can be introduced into a DNA sequence by synthesizing a sequence that has restriction enzyme cleavage terminals at both ends and contains a portion stretching over both sides of a mutation point, followed by replacing the corresponding portion of non-mutated DNA sequence with the synthesized sequence. Alternatively, the substitution, insertion or deletion can be introduced into a DNA sequence in accordance with a method such as a site-specific mutagenesis method (Kramer, W. and Frits, H. J., Meth. in Enzymol., 154, 350(1987); Kunkel, T. A. et al., Meth. in Enzymol., 154, 367(1987)). The activity to transfer sulfate group from a sulfate donor to N-acetylgalactosamine residue or galactose residue of glycosaminoglycan can be determined by e.g. enzyme activity assay as explained below, and consequently, the substitution, deletion or insertion of one of more amino acid residues which do not substantially deteriorate the activity can be easily recognized by those skilled in the art.

EXAMPLES

The present invention will now be described in more detail by way of non-limiting illustrative examples. An assay method common to all examples is explained at the beginning. If otherwise noticed, "%" means "% by weight".

(1) Enzyme Activity Assay

Sulfotransferase activity was determined as follows. The reaction solution contained, in a total volume of 50 μl, 2.5 μmol of imidazole-HCl (pH 6.8), 1.25 μg of protamine hydrochloride, 0.1 μmol of dithiothreitol, 25 nmol (as glucuronic acid) of chondroitin (available from Seikagaku Corp.), 50 pmol of [$^{35}$S] PAPS (adenosine 3'-phosphate, 5'-phosphosulfate) and an enzyme.

Activity with any of various glycosaminoglycans as a substrate was determined by replacing chondroitin with 25 nmol of the glycosaminoglycan (as galactosamine for chondroitin sulfate and dermatan sulfate; as glucosamine for heparan sulfate and keratan sulfate).

After the reaction solution was incubated at 37° C. for 20 minutes, the reaction was stopped by immersing a reaction tube in boiling water for 1 minutes. After the stop of the reaction, 0.1 μmol (as glucuronic acid) of chondroitin sulfate A was added as a carrier, then 3 volumes of ethanol containing 1.3% potassium acetate was added to precipitate $^{35}$S-labeled polysaccharide. The resultant mixture was centrifuged at 10,000×g for 10 minutes, and the obtained precipitate was dissolved in 70 μl of water. The obtained solution (50 μl) was applied to a desalting column equilibrated with 0.1M NH$_4$HCO$_3$. Eluted fractions containing $^{35}$S-labeled polysaccharide were collected. 1 ml of scintillation cocktail (Clearsol, produced by Nakarai Tesque) was added to 200 μl of each fraction to measure $^{35}$S-radioactivity, whereby the incorporation of $^{35}$S into polysaccharide was measured.

An aliquot (400 μl) was taken from the remaining solution, and to the aliquot, ethanol (800 μl) containing 1.3% potassium acetate was added and mixed. The resultant mixture was placed on ice for 30 minutes, followed by centrifugation at 10,000×g for 10 minutes to precipitate $^{35}$S-polysaccharide. The precipitate was dissolved in buffer (25 μl) containing 0.1 mg/ml of BSA, 0.05 M Tris-acetate (pH 7.5) and 10 milliunits of chondroitinase ACII (derived from *Arthrobacter aurescens*, produced by Seikagaku Corp.), and allowed to react at 37° C. for 2 hours. Reaction product was spotted onto Whatman No. 1 filter paper together with each 0.1 μmol of 2-acetamido-2-deoxy-3-O-(β-D-gluco-4-enopyranosyluronic acid)-6-O-sulfo-D-galactose (ΔDi-6S) and 2-acetamido-2-deoxy-3-O-(β-D-gluco-4-enopyranosyluroric acid)-4-O-sulfo-D-galactose (ΔDi-4S) (both produced by Seikagaku Corp.), and developed for 20 hours with 1-butanol/acetic acid/1M ammonium hydroxide (2:3:1 (V/V/V)).

Positions of ΔDi-6S and ΔDi-4S were inspected with an ultraviolet lamp. Respective sites were excised from the filter paper, and they were immersed in a scintillator prepared by dissolving diphenyloxazole (5 g) and dimethyl 1,4-bis(2-(5-phenyloxazole))benzene (0.25 g) in 1 L of toluene to measure the radioactivity. In the case of a sample digested with chondroitinase ACII, the radioactivity remaining at the origin on the filter paper was no more than 1% of the spotted radioactivity. The chondroitin 6-sulfotransferase activity and the chondroitin 4-sulfotransferase activity were calculated from the incorporation of $^{35}$S into ΔDi-6S and ΔDi-4S, respectively. The amount of activity to catalyze transfer of 1 pmol sulfate group/minute was defined as 1 unit.

The sulfotransferase activity was measured with various substrates. The results demonstrated that C6ST obtained in Example 1 transferred sulfate group to chondroitin, chondroitin sulfate derived from chick embryo cartilage, chondroitin sulfate A, chondroitin sulfate C and keratan sulfate derived from cornea, but it transferred only slightly sulfate group to chondroitin sulfate E, dermatan sulfate, and heparan sulfate. The present inventors have also confirmed that C6ST of the present invention transfers sulfate group to the C-6 position of N-acetylgalactosamine residue present in chondroitin and chondroitin sulfate, as well as transfers sulfate group to the C-6 position of galactose residue present in keratan sulfate.

Next, preparation examples of DNA of the present invention will be explained.

<1> Preparation of Chick Embryonic Chondroitin 6-sulfotransferase and Analysis of Amino Acid Sequence (1) Preparation of Chondroitin 6-sulfotransferase Chick embryo chondrocytes were inoculated to culture dishes to give a density of 5.6×10$^4$ cells/dish, and they were cultured at 38° C. for 11 days under a condition of 7 vol % CO$_2$ and 93 vol % air in Dulbecco's Modified Eagle's medium (DMEM) adjusted at pH 7.0 containing D-glucose (2 g/L), penicillin (100 units/ml), streptomycin (50 μg/ml) and 10% fetal bovine serum (FBS). The medium was exchanged for a fresh medium at pH 7.4 on the 2nd, 4th, 7th, 9th and 10th days after the start of cultivation.

A medium, containing heat-inactivated serum (10%) prepared by heating FBS at 60° C. for 60 minutes, was used on 10th day. The cells grew up to 5.0×10$^6$ cells/dish on the 11th day. After that, cultivation was continued for 10 days while exchanging the medium every day by using Cosmedium-001 (purchased from Cosmo Bio) supplemented with sodium ascorbate (50 μg/ml).

The used Cosmedium media were collected and centrifuged at 10,000×g for 10 minutes to prepare a supernatant having a composition of 10 mM Tris-HCl, pH 7.2, 0.1% Triton X-100, 20 mM MgCl$_2$, 10 mM 2-mercaptoethanol and 20% glycerol.

The culture supernatant was applied to a Heparin-Sepharose CL6B column (produced by Pharmacia LKB Biotechnology, 2.2×28 cm) equilibrated with buffer A (10 mM Tris-HCl, pH 7.2, 0.1% Triton X-100, 20 mM MgCl$_2$, 2 mM CaCl$_2$, 10 mM 2-mercaptoethanol and 20% glycerol) containing 0.15M NaCl. The column was washed with buffer A containing 0.15M NaCl, followed by elution with a linear gradient of buffer A (1 L) containing 0.15 to 0.75M NaCl to perform fractionation by 12 ml/fraction.

Fractions having the sulfotrarisferase activity were collected and applied to a wheat germ agglutinin-agarose column (produced by Seikagaku Corp., 1.2×15 cm) equilibrated with buffer A containing 0.15M NaCl. The column was washed with buffer A (200 ml) containing 0.15M NaCl, followed by elution with buffer A (200 ml) containing 0.15M NaCl and 0.3M N-acetylglucosamine. Eluted fractions were collected and dialyzed against buffer A containing 0.05M NaCl.

The dialyzed solution of the eluted fractions was applied to a 3', 5'-ADP-agarose column (produced by Sigma, 1.2×11.8 cm, 1.9 μmol 3', 5'-ADP/ml gel) equilibrated with buffer A containing 0.05M NaCl. The column was washed with buffer A (150 ml) containing 0.05 M NaCl, followed by elution with a linear gradient of buffer A (300 ml) containing 0.05M NaCl and containing 0 to 0.2 mM 3', 5'-ADP. Fractions having the sulfotransferase activity were collected and dialyzed successively against buffer A containing 1M NaCl and buffer A containing 0.05M NaCl.

The sulfotransferase activity of thus purified enzyme was measured by using the enzyme activity assay as hereinbefore described.

The results showed that the chondroitin 6-sulfotransferase had a specific activity of $4.3 \times 10^5$ units/mg and the ratio of chondroitin 4-sulfotransferase activity to chondroitin 6-sulfotransferase activity was 0.02.

Thus purified C6ST was found to form a single band on SDS-PAGE under a reducing condition and was determined to have a molecular weight of 75,000. When subjected to Superose 12 HR 10/30 gel filtration chromatography (eluent; 10 mM Tris-HCl, pH 7.2, 2M NaCl, 20 mM $MgCl_2$, 2 mM $CaCl_2$, 0.1 Triton X-100 and 20% glycerol), the same enzyme showed to have a molecular weight of 160,000. This results suggest that C6ST is forming a dimer in the presence of 2M NaCl.

It was also observed that the C6ST was activated by protamine and $MnCl_2$.

In the above assay system, the optimum pH of the C6ST was about 6.4.

(2) Analysis of Amino Acid Sequence of Chick Embryonic C6ST

Purified C6ST was digested with N-glycanase. In brief, trichloroacetic acid (200 µl) was added to 1 ml of C6ST solution (10 µg in terms of protein), and the resultant mixture was placed on ice for 30 minutes, followed by centrifugation at 10,000×g for 20 minutes. A precipitate was washed twice with 1 ml of acetone, and then dried in a vacuum desiccator. The dried C6ST protein was dissolved in 10 µl of 0.15M Tris-HCl (pH 7.8) containing 0.5% SDS, and then heated at 100° C. for 3 minutes. After cooling, 5 µl of 7.5% (w/v) Nonidet P-40, 1.2 µl of 0.25M EDTA (pH 8), 0.3 µl of phenylmethanesulfonyl fluoride, 10.5 µl of water, and 3 µl (0.75 unit) of recombinant N-glycanase (produced by Genzyme) were added. The resultant mixture was incubated at 37° C. for 12 hours for allowing to induce a deglycosylation reaction.

For the purpose of amino acid sequence analysis, after the resultant mixture was subjected to SDS-PAGE, the gel was transferred to a polyvinylidene fluoride (PVDF) membrane without staining. This membrane was stained with Coomassie Brilliant Blue. Protein bands obtained after N-glycanase digestion (49 and 47 kDa) and a band of non-digested protein (75 kDa) were excised from the membrane, and were used for amino acid sequence determination.

On the other hand, in order to determine an internal amino acid sequence of C6ST, a C6ST peptide partially digested with protease was prepared. This experiment was performed in accordance with a method of Cleveland et al. (Cleveland, D. W., Fischer, S. G., Kirshner, M. W. and Leammli, U. K. (1977) J. Biol. Chem. 252, 1102–1106). Namely, the purified protein (30 µg) was separated by SDS-PAGE using a 10% gel. After the gel was stained with Coomassie Brilliant Blue, the protein band of 75 kDa was excised, and it was inserted into a well in another 16% gel. The well was superimposed by buffer containing protease V8 (sequencing grade, produced by Boehringer Mannheim) in a ratio of 0.05 µg/µg purified protein, to start SDS-PAGE. The power source was turned off when a forward end of a dye arrived at an end of the separating gel. The electrophoresis was started again after 30 minutes. Peptides formed by the protease digestion were transblotted to a PVDF membrane. This membrane was stained with Coomassie Brilliant Blue, and then a peptide band of 19 kDa was excised.

The proteins produced after the N-glycanase digestion, the intact protein and the peptide produced after the protease V8 digestion, all of which were prepared as described above, were immobilized on PVDF filters to determine amino acid sequence of amino terminals. Results are shown in Table 1.

Table 1

49-kDa protein LVIXXXXNNFIXXV (SEQ ID NO:3)
47-kDa protein XVIXEXXNNFIXXV (SEQ ID NO:4)
Intact protein LVIXEKENNFISRVSDKLKXXPXV (SEQ ID NO:5)
19-kDa peptide SFISPAPEEXLTA (SEQ ID NO:6)

<2> Amplification of Partial cDNA of Chick Embryonic C6ST by PCR (1) Preparation of Primers for PCR In order to amplify C6ST cDNA from a cDNA library, oligonucleotide primers for PCR (Table 2) were prepared on the basis of the amino acid sequences determined as described above. Two sense primers (primers 1s and 2s) were designed on the basis of the amino acid sequence (SEQ ID NO:5) derived from the intact protein (75 kDa) of chick embryonic C6ST, whereas an antisense primer (primer 3a) was designed on the basis of the amino acid sequence (SEQ ID NO:6) derived from the protease-digested peptide (19 kDa). Each of thus designed nucleotide primers was synthesized.

Table 2 primer 1s CAAAGCTTGA RAARGARAAY AAYTTYAT (SEQ ID NO:7)
primer 2s MGKGTKWSKG AYAARCTNAA (SEQ ID NO:8)
primer 3a AARTADWSKG GKCGKGGKCT TCTTAAGCT (SEQ ID NO:9)

A nucleotide sequence containing a HindIII recognition sequence was introduced into the 5'-end of the primer 1s, whereas a nucleotide sequence containing an EcoRI recognition sequence was introduced into the 5'-end of the primer 3a.

(2) Preparation of Poly(A)+ RNA

Total RNA was prepared by the guanidine thiocyanate/CsCl method (Kingston, R. E., (1991) in Current Protocols in Molecular Biology, Suppl. 14, Unit 4.2 Greene Publishing Associates and Wiley Interscience, New York) by starting from chick embryo chondrocytes which had been cultured for 11 days in Dulbecco's Modified Eagle's medium (DMEM) containing 10% fetal bovine serum in accordance with a known method (Kim, J. J. and Conrad, H. E. (1976) J. Biol. Chem. 251, 6210–6217; Kim, J. J. and Conrad, H. E. (1977) J. Biol. Chem. 252, 8292–8299; Kim, J. J. and Conrad, H. E. (1980) J. Biol. Chem. 255, 1586–1597). The obtained total RNA was purified by oligo(dT) cellulose column chromatography to obtain poly(A)+ RNA.

(3) PCR (Polymerase Chain Reaction)

By using the above obtained poly(A)+ RNA as a template and the oligonucleotide 3a as a primer, a primary cDNA strand was synthesized by the reverse transcription reaction. For the reverse transcription, the reaction was carried out by incubating at 37° C. for 60 minutes a buffer that contained, in a final volume 20 µl, poly(A)+ RNA (1 µg), oligonucleotide 3a (50 pmol), 4 different deoxynucleoside triphosphates (500 µM each), M-MLV reverse transcriptase (200 units, produced by Gibco BRL), 1 mM dithiothreitol and RNase inhibitor (120 units, produced by Takara Shuzo).

For PCR, the reaction was carried out in a reaction solution that contained, in a final volume of 100 µl, the above defined mixture (10 µl) for reverse transcription, oligonucleotides 1s and 3a (50 pmol each), 4 different deoxynucleoside triphosphates (100 µM each) as well as Taq polymerase (2.5 units, AmpliTaq polymerase, produced by Perkin-Elmer). The amplification cycle was repeated 30 times, each cycle being composed of 1 minute at 94° C., 1 minute at 45° C. and 3 minutes at 55° C.

<3> Preparation of Entire Length cDNA of Chick Embryonic C6ST (1) Preparation of Hybridization Probe The obtained PCR-amplified fragment was recovered, digested with HindIII and EcoRI; and subcloned into a plasmid vector, Bluescript (produced by Stratagene), at the sites cleaved with these restriction enzymes. A subclone was confirmed by sequencing with the aid of T3 primer or M13–20 primer.

A radioactive probe for screening a cDNA library was obtained by radiolabeling the aforesaid PCR product in accordance with a random olignucleotide-primed labeling method (Feinberg, A. P. and Vogelstein, B. (1983) Anal. Biochem. 132, 6–13) using $[\alpha\text{-}^{32}P]$ dCTP (produced by Amersham) and a DNA random labeling kit (produced by Takara Shuzo).

(2) Construction of cDNA Library

Next, in order to obtain cDNA containing an entire length of the coding region of C6ST, a lambda vector, $\lambda$gt11, was used to perform cDNA cloning.

Poly(A)+ RNA was prepared from chick embryo chondrocytes in the same manner as described above in <2> (2), and was used as a template to synthesize a double-stranded cDNA. The DNA was ligated into EcoRI-digested $\lambda$gt11 (produced by Pharmacia). A cDNA synthesis kit (TimeSaver cDNA synthesis kit, produced by Pharmacia) was used for the synthesis of cDNA and the ligation into the vector. Random oligonucleotide primers were used as a primer for the reverse transcription reaction.

The recombinant phage vector with inserted cDNA was packaged into phage particles by using an in vitro packaging kit (Gigapack II packaging extract, produced by Stratagene). *Escherichia coli* Y1088 was infected with these phage particles and was layered on a plate to form plaque. A phage library thus obtained was used for cDNA screening without further amplification.

(3) Screening of C6ST cDNA clone

Screening was performed of about 5×10 plaques of the $\lambda$gt11 cDNA library obtained as described above. Plaques were transferred onto a commercially available nylon membrane (Hybond N+ nylon membrane, produced by Amersham), and phage DNA was immobilized onto the nylon membrane by using an alkaline immobilizing method according to the manufacturer's recommendations appended to the commercial product.

The membrane having immobilized phage DNA thereon was subjected to prehybridization at 42° C. for 3.5 hours in a solution containing 50% formamide, 5× SSPE (composition of 1× SSPE: 10 mM $NaH_2PO_4$ (pH 7.4), 150 mM NaCl, 1 mM EDTA), 5× Denhardt's solution (composition of 1× Denhardt's solution: 0.02% Ficoll 400, 0.02% polyvinylpyrrolidone, 0.02% BSA), 0.5% SDS, 0.04 mg/ml of denatured salmon sperm DNA, and 0.004 mg/ml of *E. coli* DNA. Hybridization was performed at 42° C. for 16 hours in the same buffer as described above containing the $^{32}P$-labeled probe. After that, the filter was washed at 55° C. successively in 1× SSPE (0.1% SDS) and in 0.1× SSPE (0.1% SDS), and thereafter hybridization-positive clones were detected by means of autoradiography. About 90 positive clones were obtained from 5×10$^5$ plaques.

(4) Nucleotide Sequence Analysis of Chick Embryonic C6ST cDNA

Sixteen independent clones were selected from the hybridization-positive $\lambda$gt11 clones. Respective phage DNA was prepared and digested with EcoRI to excise cDNA insertion fragment as a single fragment from the vector DNA. The obtained DNA fragments were subcloned into Bluescript. Among these DNA fragments, the nucleotide sequence of the longest fragment (2.3 kb) was determined.

From the recombinant plasmid obtained by subcloning cDNA into Bluescript, a deletion clone was prepared by using a DNA deletion kit (produced by Takara Shuzo) in accordance with a known method (Henikoff, S. (1984) Gene 28, 351–359; Yanisch-Perron, C., Viera, J., and Messing, J. (1985) Gene 33, 103–109). Restriction enzymes, SacI and XbaI, were used for leaving 3'-cohesive end and a 5'-cohesive end respectively.

The obtained deletion clone was subjected to dideoxy chain termination method (Sanger, F., Nicklens, S., and Coulson, A. R. (1977) Proc. Natl. Acad. Sci. U.S.A. 74, 5463–5467) by using $\alpha$-$^{32}P$) dCTP and T7 DNA polymerase (Sequenase, produced by U.S. Biochemicals), to determine the nucleotide sequences of both strands independently.

<4> Cloning of Human C6ST cDNA (1) Preparation of Hybridization Probe

From the chick embryonic C6ST cDNA obtained in the preceding step <3> (4), an $[\alpha\text{-}^{32}P]$ dCTP-labeled radioactive probe for cDNA library screening was prepared by random primer labeling method. More specifically, the aforementioned chick cDNA was radiolabeled in accordance with a random olignucleotide-primed labeling method (Feinberg, A. P. and Vogelstein, B. (1983) Anal. Biochem. 132, 6–13) using $[^{32}P]$ dCTP (produced by Amersham) and DNA random labeling kit (produced by Takara Shuzo).

(2) Construction of Human cDNA Library

In order to obtain a cDNA containing an entire length of the coding region of human C6ST, human fetal brain cDNA library (available from Clontech) integrating a lambda vector, $\lambda$gt11, was used.

The recombinant phage vector with inserted cDNA was packaged into phage particles by using an in vitro packaging kit (Gigapack II packaging extract, produced by Stratagene). *Escherichia coli* Y1088 was infected with these phage particles and was layered on a plate to form plaque. A phage library thus obtained was used for cDNA screening without further amplification.

(3) Screening of C6ST cDNA Clone

Screening was performed from the plaques of the $\lambda$gt11 cDNA library in the same manner as described in the foregoing step <3> (3). Namely, plaques were transferred onto a commercially available nylon membrane (Hybond N+ nylon membrane, produced by Amersham), and phage DNA was immobilized onto the nylon membrane in accordance with an alkaline immobilizing method.

The membrane having immobilized phage DNA thereon was subjected to prehybridization at 42° C. for 3.5 hours in a solution containing 50% formamide, 5× SSPE, 5× Denhardt's solution, 0.5% SDS, 0.04 mg/ml of denatured salmon sperm DNA, and 0.004 mg/ml of *E. coli* DNA. Hybridization was performed at 42° C. for 16 hours in the same buffer as described above containing the $^{32}P$-labeled probe. After that, the filter was washed at 55° C. successively in 1× SSPE (0.1% SDS) and in 0.1× SSPE (0.1% SDS), and thereafter, hybridization-positive clones were detected by means of autoradiography.

(4) Nucleotide Sequence Analysis of C6ST cDNA

Independent clones were selected from the hybridization-positive $\lambda$gt11 clones obtained as above. Each phage DNA was prepared and digested with EcoRI to excise cDNA insertion fragment as a single fragment from the vector DNA. The obtained DNA fragments were subcloned into Bluescript.

Recombinant plasmid obtained by subcloning cDNA into Bluescript was treated with DNA deletion kit (produced by Takara Shuzo) according to a known method (Henikoff, S. (1984) Gene 28, 351–359; Yanisch-Perron, C., Viera, J., and Messing, J. (1985) Gene 33, 103–109), to prepare a deletion clone.

The obtained deletion clone was treated with [$\alpha$-$^{32}$P] dCTP and T7 DNA polymerase (Sequenase, produced by U.S. Biochemicals) in accordance with dideoxy chain termination method (Sanger, F., Nicklens, S., and Coulson, A. R. (1977) Proc. Natl. Acad. Sci. U.S.A. 74, 5463–5467), to determine the nucleotide sequences of both strands independently. The nucleotide sequence which corresponds to the open reading frame of human C6ST cDNA thus determined is shown in SEQ ID NO:1, and the amino acid sequence deduced therefrom is shown in SEQ ID NO:2.

The determined DNA sequence was analyzed by using Gene Works computer programs (produced by IntelliGenetics). Two in-frame ATG codons are contained in a 5'-terminal portion of an open reading frame of C6ST cDNA. A single open reading frame starting from the first ATG codon suggests a protein containing 479 amino acid residues with a molecular weight of 54,610. This protein was found to have 74% amino acid sequence homology with the abovementioned chick C6ST. In particular, human C6ST obtained according to the present invention had a highly hydrophilic, specific insertion sequence composed of 17 amino acids (amino acids numbered from 114 to 130 of SEQ ID NO:2) which was absent in chick C6ST.

(5) Construction of Human C6ST Expression Plasmid

In order to express human C6ST cDNA, the cDNA fragment was introduced into an expression vector to construct a recombinant plasmid. An expression vector for mammalian cells, pCXN2 (constructed by Dr. Jun-ichi Miyazaki of the University of Tokyo (Niwa, H., Yamamura, K., and Miyazaki, J. (1991) Gene 108, 193–200) and kindly given by Dr. Yasuhiro Hashimoto of Tokyo Metropolitan Institute of Medical Science), was used as the expression vector. pCXN2 is a vector which has a streptomycin-resistant gene and a penicillin-resistant gene, and can express a DNA fragment inserted into an EcoRI site with the aid of a $\beta$-actin gene promoter. The cDNA fragment of 2,354 bp (SEQ ID NO:1) was ligated to the EcoRI site of pCXN2. E. coli JM109 was transformed with a reaction solution after the ligation, and it was applied onto an LB plate containing ampicillin. Recombinant plasmids were recovered from transformants, and they were purified by three times of CsCl/ethidium bromide equilibrium centrifugation. A recombinant plasmid, in which the promoter of the vector and cDNA had a coincident direction, was designated as pCXNhC6ST. A recombinant plasmid, in which cDNA was inserted in an opposite direction, was designated as pCXNhC6ST2. The direction of cDNA was analyzed by restriction mapping by using BamHI.

(6) Transient Expression of Human C6ST cDNA in COS-7 Cells

COS-7 cells were used as a host for expressing human C6ST cDNA. COS-7 cells (obtained from RIKEN CELL BANK, Tsukuba) were sown on culture dishes having a diameter of 100 mm at a density of $8 \times 10^5$ cells/dish. Dulbecco's Modified Eagle's medium (DMEM) containing penicillin (100 units/ml), streptomycin (50 $\mu$g/ml), and 10% fetal bovine serum (produced by Gibco BRL) was used as a culture liquid in an amount of 10 ml per culture dish. Cells were cultured in 5 vol % of $CO_2$ and 95 vol % of air at 37° C.

COS-7 cells were transfected with pCXNh(6ST or pCXNhC6ST2 after 48 hours of cultivation. The transfection was performed in accordance with the DEAE-dextran method (Aruffo, A. (1991) in Current Protocols in Molecular Biology, Suppl. 14, Unit 16. 13, Greene Publishing Associates and Wiley Interscience, New York). Previously warmed DMEM (5 ml) containing 10% Nu serum (a serum substitute having a low protein concentration, produced by Collaborative Biomedical Products) was mixed with PBS (phosphate-buffered saline, 0.2 ml) containing DEAE dextran (10 mg/ml) and chloroquine solution (2.5 mM). This solution was mixed with 15 $\mu$g of the recombinant plasmid, and a resulting mixture was added to the cell suspension.

The cells were incubated for 4 hours in a $CO_2$ incubator. After that, the culture liquid was substituted with a PBS solution (5 ml) containing 10% dimethyl sulfoxide. The cells were left at room temperature for 2 minutes. After that, the dimethyl sulfoxide solution was removed by aspiration, followed by addition of 25 ml of DMEM containing penicillin (100 units/ml), streptomycin (50 $\mu$g/ml), and 10% fetal bovine serum. The cells were incubated for 67 hours, and then they were washed with only DMEM. The cells were collected and homogenized by using Dounce homogenizer in a solution containing 0.25M sucrose, 10 mM Tris-HCl, pH 7.2, and 0.5% Triton X-100, the solution being used in an amount of 1.5 ml for cells obtained from one culture dish. An obtained homogenate was centrifuged at 10,000×g for 20 minutes to measure the C6ST activity, the chondroitin 4-sulfotransferase (C4ST) activity, and the keratan sulfate sulfotransferase (KSST) activity in a supernatant fraction. These activities were measured in the presence or absence of chondroitin or keratan sulfate as a sulfate group acceptor. As for COS-7 cells which had not been transfected with the expression plasmid, the measurement was performed in the same manner as described above. Results are shown in Table 3.

TABLE 3

| Plasmid | C6ST activity | C4ST activity | KSST activity |
|---|---|---|---|
|  | (pmol/minute/mg protein) | | |
| None | 6.4 ± 2.5 | 0.8 ± 0.2 | 2.0 ± 0.3 |
| pCXNhC6ST2 | 5.7 ± 1.2 | 0.9 ± 0.2 | 1.5 ± 0.2 |
| pCXNhC6ST | 102.4 ± 3.5 | 4.7 ± 1.0 | 30.5 ± 2.1 |

As shown in Table 3, the C6ST activity and the KSST activity of the cells harboring the expression vector to express the aforementioned isolated cDNA in the correct direction were about 16-fold and about 20-fold respectively as compared with those of the cells harboring the expression vector with cDNA inserted in the opposite direction. In contrast, the C4ST activity of the transfected cells was increased only slightly. These results have proved that the isolated cDNA codes for a protein having the C6ST activity and the KSST activity.

What is claimed is:

1. An isolated DNA coding for a polypeptide having a glycosaminoglycan sulfotransferase activity, said polypeptide originating from humans and having the following properties:

(i) action: sulfate group is transferred from a sulfate group donor to N-acetylgalactosamine residue or galactose residue of glycosaminoglycan; and (ii) substrate specificity: sulfate group is transferred to the hydroxyl group position at C-6 of N-acetylgalactosamine residue of chondroitin; and sulfate group is transferred to the hydroxyl group position at C-6 of galactose residue of keratan sulfate.

2. An isolated DNA which has a nucleotide sequence coding for the amino acid sequence represented by amino acid numbers 1 to 479 of SEQ ID NO:2.

3. An isolated DNA which has a nucleotide sequence coding for the amino acid sequence represented by amino acid numbers 20 to 479 of SEQ ID NO:2.

4. The DNA according to claim 2, which has at least a part or the whole of the nucleotide sequence represented by nucleotide numbers 147 to 1583 of SEQ ID NO:1.

5. The DNA according to claim 3, which has at least a part or the whole of the nucleotide sequence represented by nucleotide numbers 204 to 1583 of SEQ ID NO:1.

6. The DNA according to claim 1, wherein said polynucleotide has a nucleotide sequence represented by nucleotide numbers 147 to 1583 of SEQ ID NO:1.

7. The DNA according to claim 1, wherein said polynucleotide has a nucleotide sequence represented by nucleotide numbers 204 to 1583 of SEQ ID NO:1.

* * * * *